United States Patent [19]

van Krieken

[11] Patent Number: 5,522,857
[45] Date of Patent: Jun. 4, 1996

[54] PACEMAKER WITH IMPROVED DETECTION OF AND RESPONSE TO NOISE

[75] Inventor: Frits M. van Krieken, Dieren, Netherlands

[73] Assignee: Vitatron Medical, B.V., Dieren, Netherlands

[21] Appl. No.: 309,072

[22] Filed: Sep. 20, 1994

[51] Int. Cl.$^6$ ........................................... A61N 1/36
[52] U.S. Cl. ........................... 607/9; 607/14; 607/25
[58] Field of Search ........................... 128/901; 607/9, 607/14, 16

[56] References Cited

U.S. PATENT DOCUMENTS

| | | | |
|---|---|---|---|
| 3,972,334 | 8/1976 | Wickham | 607/9 |
| 4,043,347 | 8/1977 | Renirie | 128/419 PG |
| 4,129,133 | 12/1978 | Irnich et al. | 607/9 |
| 4,379,459 | 4/1983 | Stein | 128/419 PG |
| 4,432,362 | 2/1984 | Leckrone et al. | 607/9 |
| 4,941,471 | 7/1990 | Mehra | 607/9 |
| 5,247,930 | 9/1993 | Begemann et al. | 607/11 |

*Primary Examiner*—William E. Kamm
*Assistant Examiner*—Carl H. Layno
*Attorney, Agent, or Firm*—Woodcock Washburn Kurtz Mackiewicz & Norris

[57] ABSTRACT

A pacemaker system and method are provided with an improved way of detecting the presence of noise, and particularly intermittent noise. When a first signal is sensed by the pacemaker sense circuit, the pacemaker schedules and starts to time out a next escape interval while continuing to time out the escape interval which was previously set. The pacemaker sets up a predetermined noise interval and continues to monitor senses, for the purpose of determining whether the first sense is to be treated as a true cardiac signal, or as noise. In the preferred embodiment, if a second sense occurs within the noise interval, and before time out of a minimum pacing interval, the first sense is determined to be noise, and the pacemaker continues to time out the initial escape interval; however, if no additional sense occurs during the noise interval, the pacemaker proceeds to time out the previously set next escape interval. In the case of a second sense within the noise interval but after time out of the minimum pacing interval, the second sense triggers a safety pace, to protect from continuous inhibition by pulsed noise.

8 Claims, 7 Drawing Sheets

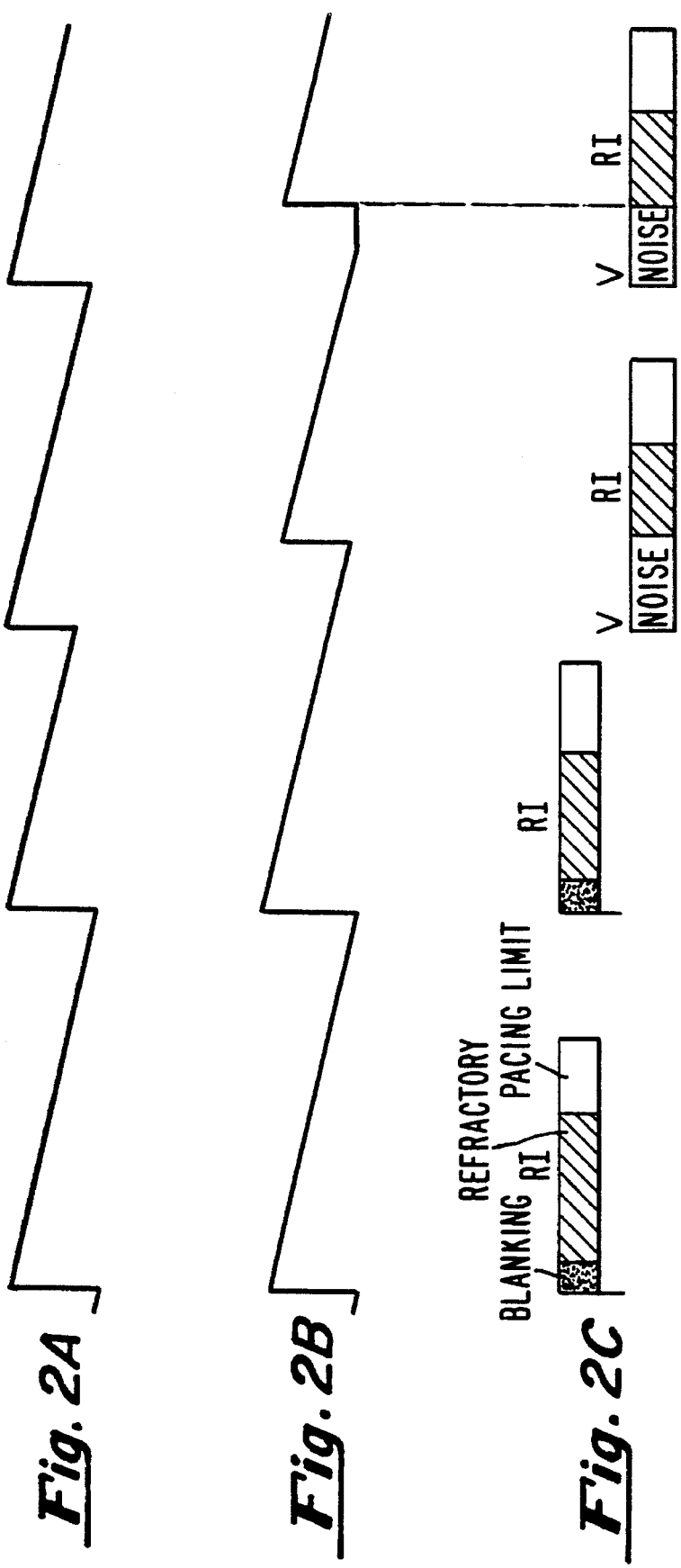

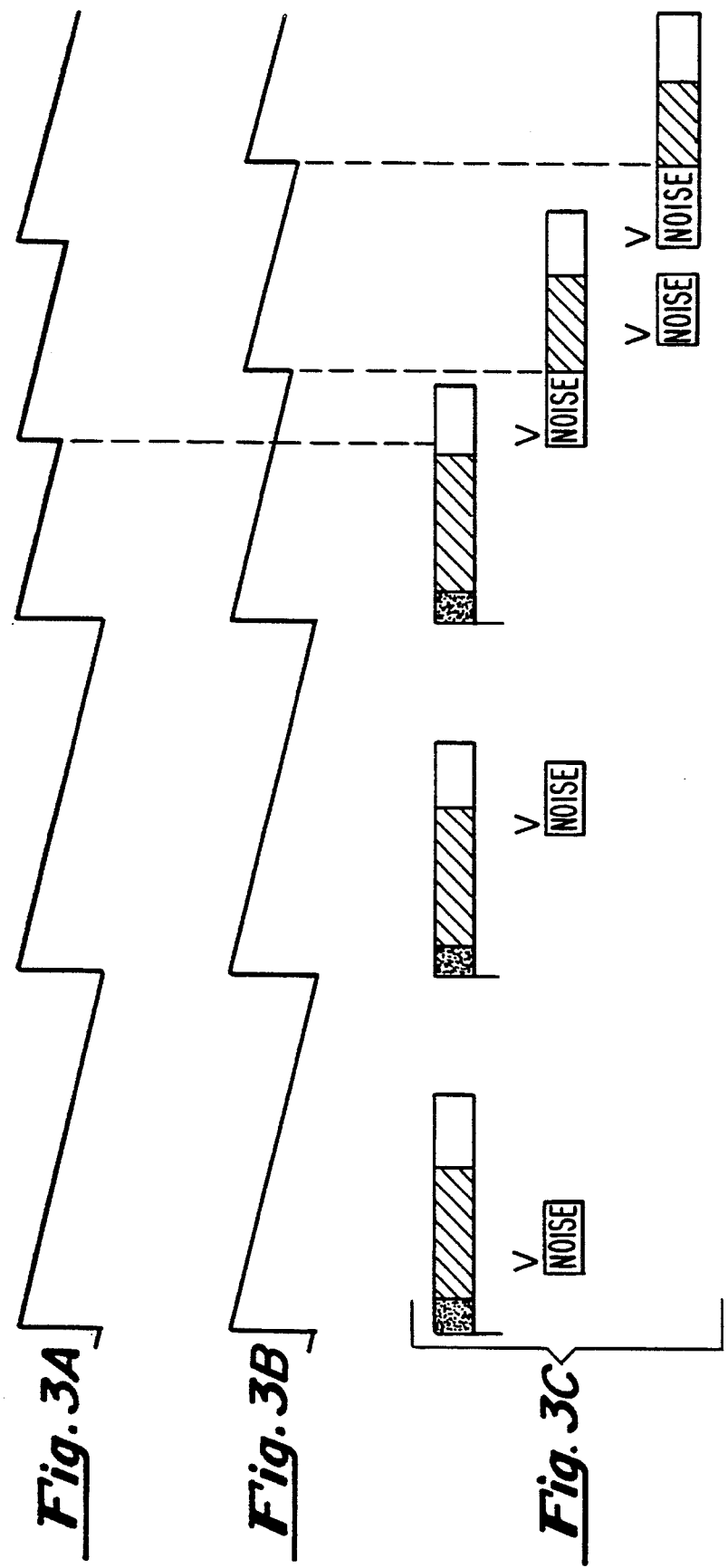

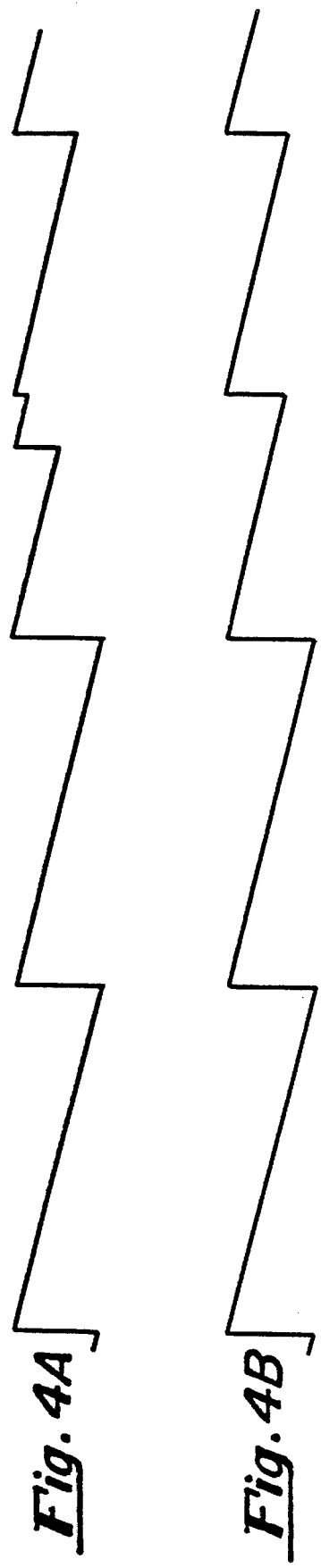
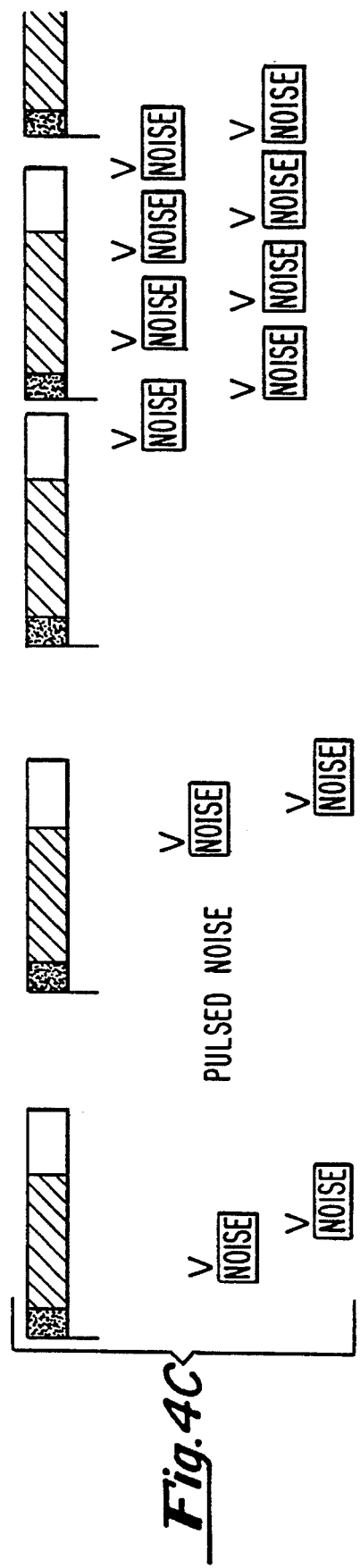
Fig. 4A
Fig. 4B
Fig. 4C

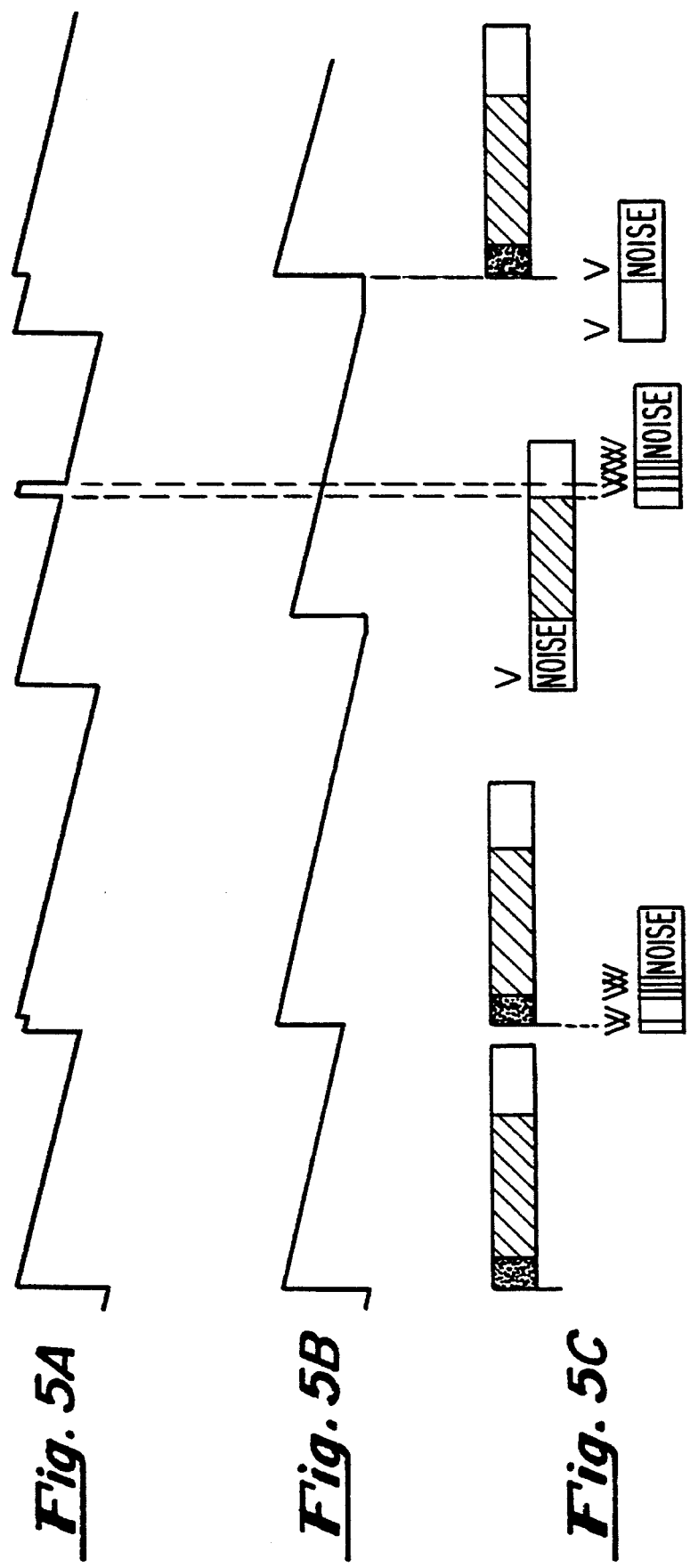

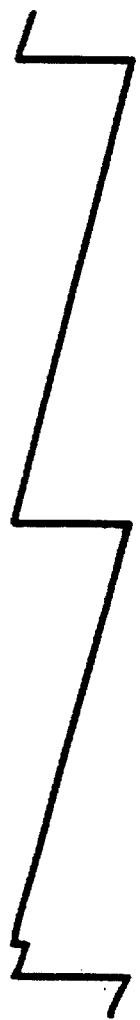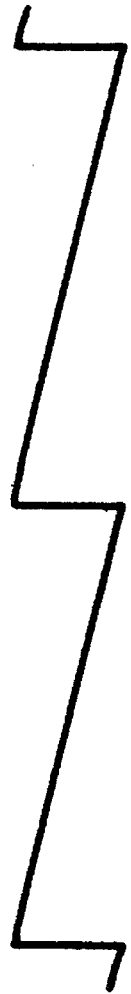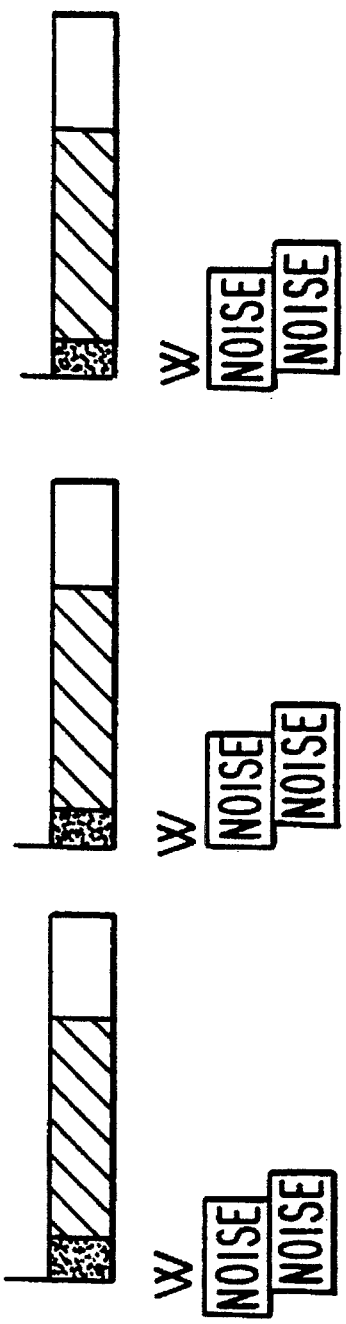
Fig. 7A
Fig. 7B
Fig. 7C

PACEMAKER WITH IMPROVED DETECTION OF AND RESPONSE TO NOISE

BACKGROUND OF THE INVENTION

1. Field of the Invention

This invention relates to cardiac pacemakers and, more particularly, to implantable cardiac pacemakers with automatic means for discriminating between intermittent noise and true sensed cardiac signals.

2. Description of the prior Art

For virtually the entire lifetime of the cardiac pacemaker industry, there has been a need to make pacemakers more invulnerable to sensing externally generated noise. With the advent of the demand pacemaker, pacemakers have included a sensing circuit for sensing natural heartbeats, so as to inhibit delivery of pace pulses in the presence of naturally occurring beats. But such a sense circuit inherently is able to pick up other signals as well, and it has thus been necessary to design protection into the pacemaker so that externally generated noise of any nature is not interpreted as heartbeats.

There have been many approaches to the problem of discriminating noise from true cardiac signals. The filter characteristics of the sense amplifier can be adapted to maximize detection of the cardiac signal—either the QRS or P wave—while filtering out signals that have characteristics more similar to noise. See also U.S. Pat. No. 4,379,459, which discloses a pacemaker with detection circuitry that senses intrinsic heart signals in the presence of very large amplitude repetitive noise signals. Another long used approach is disclosed in U.S. Pat. No. 4,043,347. This reference illustrates the standard noise suppression technique of resetting a flipflop, or other logic circuitry, upon the detection of noise, so as to extend the pacemaker refractory interval and thereby prevent the pacemaker from acting on early signals which could be noise. In such an arrangement the detection of continuous noise prevents any signal from the sense amplifier from resetting the refractory interval, such that substantially continuous noise results in fixed rate pacing. However, this arrangement cannot accurately respond to discontinuous, or intermittent noise of many varieties, e.g., noise spikes that are detected after the refractory interval.

The above problems take on more urgency in view of the Cenelec standard for safe pacing during intermittent noise. What is needed is a more reliable noise detection arrangement for handling intermittent as well as continuous forms of noise, and determining when a sense signal can be treated as a true intrinsic cardiac signal and when it must be treated as noise.

SUMMARY OF THE INVENTION

It is an object of this invention to provide a pacemaker system with a reliable means for determining when the sense signals truly indicate depolarization signals from the patient's heart, and when such sense signals are in fact noise and cannot be used for control of the pacemaker. Such a reliable means of distinguishing noise and intrinsic cardiac signals is provided by having two effective timers, e.g., a first timer for timing out a scheduled escape interval at the start of each pacemaker cycle; and a second timer which acts as a redundant or background timer, and which is likewise reset to time out the escape interval at the true start of each pacemaker cycle, but which is subject to different rules for being reset. The first timer is reset to its starting value following any first sense following the refractory period, which first sense is assumed to be a depolarization. The second timer is not reset by the first sense, but waits for the pacemaker to analyze additional sensed signals which occur subsequent to the first sense but before timeout of the scheduled escape interval. If, during this subsequent analysis period, the first sense is determined to have been a true depolarization, the background timer is reset to the value of the main timer, such that the new pacemaker cycle is deemed to have started with the first sense. However, if one or more subsequent senses occur with a timing that indicates that the first sense was noise, the main timer is returned to the value of the background timer so that the pacemaker continues to time out the scheduled escape interval of the first cycle. However, in order to protect against continuous inhibition pulsed noise, a pace pulse is provided upon the determination that the first sense was noise if the second sense occurs after a minimum pacing interval.

In a preferred embodiment, the logic for determining whether the initial sense was noise or a true cardiac signal is based upon initiating a noise interval or interference delay of predetermined time duration, e.g., 110 ms, and if another signal is sensed before the timeout of this interval, the initial sense is determined to have been noise. At the time of receiving the subsequent signal before timeout of the noise interval, the pacemaker checks to see whether the duration from the start of the cycle exceeds a predetermined minimum pacing interval, corresponding to a high rate limit. If the minimum pacing interval has not yet timed out, the main timer is reset to the background timer. However, if the minimum pacing interval has timed out, then a pace pulse is delivered and both the main timer and the background timer are reset to their starting value, thereby starting a new pacemaker cycle. The pacemaker thus provides both good noise detection and suppression, and a safe method of safety pacing.

BRIEF DESCRIPTION OF THE DRAWINGS

FIGS. 2A, B, and C are diagrams representing respectively (a) the value with respect to time of the main escape timer, (b) the value with respect to time of the background escape timer, and (c) marker channel designations representing sense and pace events, and the timeout of different intervals by the pacemaker.

FIGS. 3A, B, and C are curves of the same nature as FIGS. 2A–2C for a different sequence of events, namely separate sense signals occurring at different respective times during pacemaker cycles.

FIGS. 4A, B, and C are curves of the same nature as FIGS. 2A–2C for a different sequence of events, e.g., showing two cycles of pulsed noise and three cycles of continuous noise.

FIGS. 5A, B, and C are curves of the same nature as FIGS. 2A–2C for a different sequence of events, e.g., an example of bursts of noise, as well as an example where the pacemaker logic results in delivering a pace pulse slightly later than timeout of the original escape interval.

FIGS. 7A, B, and C are curves of the same nature as FIGS. 2A–2C for a different sequence of events, e.g., where the events constitute sensed pairs occurring cyclically, causing the pacemaker to effectively operate in a triggered mode.

DESCRIPTION OF THE PREFERRED EMBODIMENTS

Figure 1A:
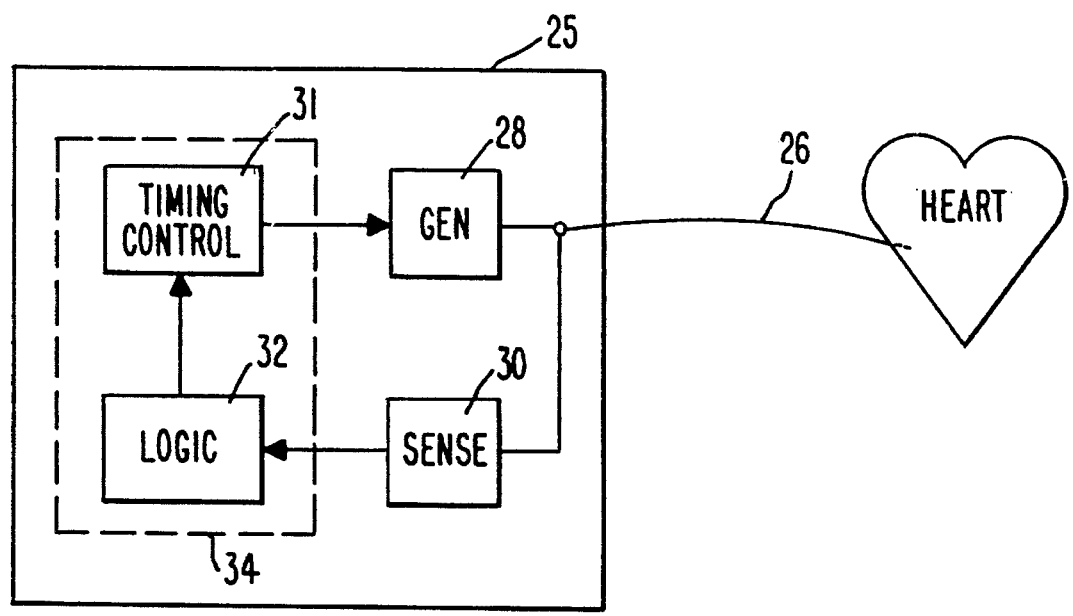
FIG. 1A is a block diagram indicating the primary components of the pacemaker system of this invention.

Referring to FIG. 1A, there is shown a simplified block diagram of the primary components of the pacemaker system of this invention. The pacemaker 25 is illustrated in combination with a lead 26. Lead 26 delivers pace pulses from pulse generator 28 to the heart, and delivers signals sensed in the heart to sense circuitry 30. As illustrated, the pacemaker is described as a single chamber pacemaker, e.g., VVI or AAI. Also shown in pulse control block 34, which receives signals from sense circuit 30 and provides control signals to generator 28. Block 34 comprises logic circuitry 34, which determines when condition require either triggering a pace pulse or starting a new pacemaker cycle without delivery of a pace pulse. And timing control block 31 acts upon the output of block 32 to generate a control signal appropriate for controlling the parameters of each pace pulse, i.e., timing, pulse width, pulse level, etc.

Figure 1B:
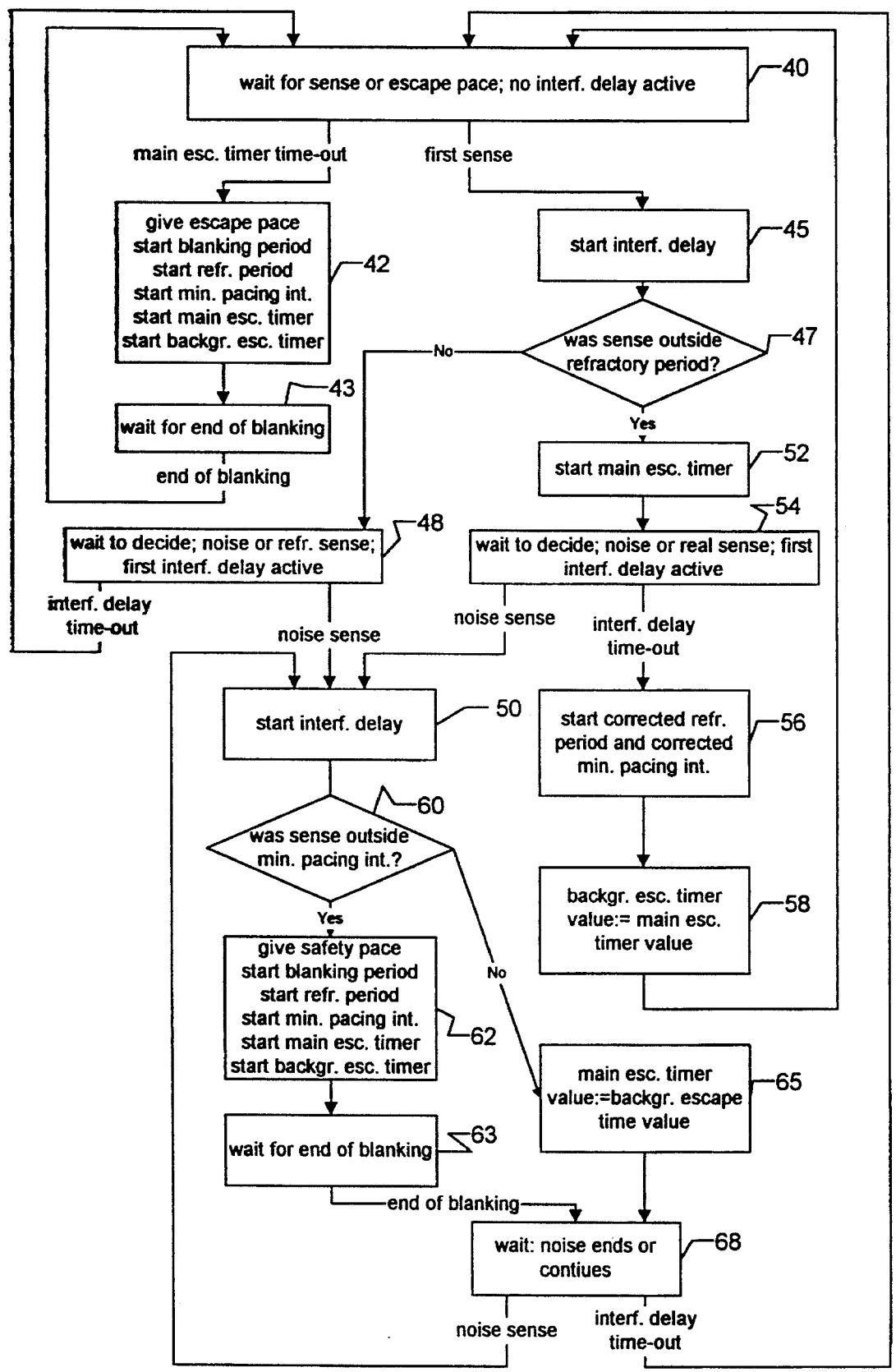
FIG. 1B is a flow diagram showing the main components of the logic for controlling the pacemaker and for determining whether sense signals are true intrinsic cardiac signals, or are noise. The logic determinations of FIG. 1B can be carried out by hardware or software, or a combination of hardware and software.

The pacemaker components illustrated in FIG. 1 are well known in the art, and can be provided by using all hardware or a combination of hardware and software. Many modem pacemakers incorporate a microprocessor with memory, for carrying out pacemaker logic and timing functions, and software is preferred for use in this invention. Also, it is noted that many other features such as external programmability of operating parameters, internal data storage and read out, automatic rate control, and the like, may be incorporated. Before referring to the detail presented by FIG. 1B, the main elements of the invention can first be summarized. The improved noise detection, and response to noise detection, are based upon reacting to a sensed signal—also referred to as simply a "sense"—by preparing for a subsequent logical determination that the sense was either a true signal, or was noise. Thus, the pacemaker is enabled to either react by resetting its timing to start a new cycle, as when the sense is a depolarization; or to react by continuing the timing of the current cycle, or by delivering a triggered pace. The pacemaker prepares for either determination, and waits to analyze subsequent events (or lack of events) before proceeding with the proper reaction. The basic building blocks specifically required to carry out this arrangement are:

i. a blanking period after a pace, to prevent sensing of pacing artifacts and evoked responses;

ii. a refractory period after a pace and after a sense;

iii. a time duration extended beyond the refractory interval, defining the allowed minimum pacing interval (MPI), corresponding to an upper pacing rate limit. The duration of MPI beyond the refractory interval may be zero, so that MPI=RI; this is particularly meaningful in triggered modes (AAT, VVT) since then the allowable minimum intervals for both noise and regular triggered senses are equal.

iv. a noise interval (NI), or interference delay, of about 100 to 110 ms;

v. a main escape timer to time out the escape interval;

vi. a background escape timer to time out the escape interval; and vii. logic for setting and resetting the two timers in accordance with the sequence of sense and pace events.

The rules governing the operation of the pacemaker of this invention, for VVI or AAI pacing, are as follows:

Rule 1. Any pace resets the main and background escape timers and starts a blanking period, a refractory interval and a minimum pacing interval.

Rule 2. No sensing is possible during a blanking period.

Rule 3. When no Noise Interval is active, i.e., is being timed out, any sense outside the refractory interval resets the main escape timer.

Rule 4. When no Noise Interval is active, any sense starts a Noise Interval.

Rule 5. When a Noise Interval times out without retriggering, the sense is determined to have been a depolarization, i.e., a true cardiac signal; when this sense was outside the refractory interval, a new refractory interval and an additional minimum pacing interval are set up, with correction for the past Noise Interval.

Rule 6. When a Noise Interval is already active (due to a prior sense), a new sense retriggers the Noise Interval, indicating that noise has been detected (determined); no new refractory interval or minimum pacing interval is set up.

Rule 7. Upon any retriggering of the Noise Interval, a pace is delivered unless it would violate the minimum pacing interval corresponding to a previous pace or sense (i.e, come before the time out of the MPI); when no pace is delivered, the main escape timer is made equal to (set to the same value of remaining time as) the background escape timer.

Rule 8. When a first Noise Interval is caused by a nonrefractory sense and times out without being retriggered, the background escape timer is made equal to the main escape timer.

Rule 9. A pacing pulse is delivered when the main escape timer times out.

Rule 10. When the background escape timer times out it remains at its time out value (e.g., zero) and is not reset (it is only set to equal the main timer value at a subsequent time out of a Noise Interval, or reset to its full starting value upon delivery of a pace pulse).

Referring now to FIG. 1B, there is shown a flow diagram for execution of the above rules. As used in the discussion, the timers are considered to start at the value corresponding to a given interval, and time out to zero. Thus, for an escape interval of 900 ms, the timer is set, or reset, to 900 ms at the start of a cycle, and commences the period of timing out; it times out when it reaches zero. As is understood, and as the term is used in the claims, a timer is "timing out" as it proceeds toward zero, even though it may be reset to its starting value before it times out to zero.

Referring now to FIG. 1B, at block 40 the pacemaker waits to determine whether there has been a sensed signal or the escape interval has timed out. During this time, typically at the start of the pacemaker cycle, there is no interference delay active. If the main escape timer has timed out, the routine goes to block 42. A pace pulse is delivered, and then the pacemaker starts a new blanking period; starts the refractory period; starts the minimum pacing interval; starts the main escape timer; and starts the background escape timer. Then at block 43 the pacemaker waits for end of blanking, following which it returns to block 40.

If, at block 40, there is a sense before time out of the escape timer, the routine goes to block 45 and starts the interference delay, typically 110 ms. Then, at block 47 it determines whether the first sense was outside the refractory interval. If no, meaning that it came during the refractory interval, the routine branches to block 48 where the pacemaker waits to decide whether there is continuing noise or whether this was a single refractory sense; the first interference delay is still active. If this interference delay times out, the routine exists back to block 40. If another signal is sensed within the interference delay, the routine goes to block 50, where another interference delay is started.

Returning to block 47, if the sense was outside the refractory period, the routine goes to block 52 and starts, or resets the main escape timer. Thus, at this point, the pacemaker is assuming that the sense was a true cardiac sense, which assumption holds until and only if it is later determined that it was noise. At block 54, the pacemaker waits to decide whether it was noise or a true sense, setting the fist interference delay active. If it was a noise sense, the routine branches to block 50. If, however, at 54 the wait terminates in timeout of the interference delay, the routine goes to block 56 and starts a corrected refractory period and corrected minimum pacing interval. Then, at 58, the background escape timer is set equal to the value of the main escape timer, and the routine returns to block 40.

Returning to block 50, where a second interference delay has been set due to a noise sense, the routine then goes to block 60 and determines whether the noise sense was outside the MPI. If yes, at 62 the pacemaker produces a safety pace pulse. It also starts a new blanking period, a refractory period, minimum pacing interval, and starts both the main escape timer and the background escape timer from their starting values. Then at 63 the pacemaker waits for end of blanking, and then goes to block 68. At 68, if there is another noise sense within the interference delay, the routine branches back to block 50. However, if the interference delay times out, the routines branches back to block 40. Returning to block 60, if the sense was not outside the minimum pacing interval, the pacemaker, at block 65, sets the value of the main escape timer to the value of the background escape timer. Then the routine goes to block 68, and waits to determine whether the noise ends or continues, as set forth above.

Referring now to FIGS. 2A, B, C, FIG. 2A shows a first waveform representative of the value of the main escape timer; FIG. 2B shows a second waveform representative of the background escape timer; and FIG. 2C shows a timing diagram expressed in marker channel symbols, the two waveforms in the timing diagram corresponding to the sensed events indicated in FIG. 2C. As shown in FIG. 2C, the dark portion of the linear marker channel following a pace pulse represents the blanking period, during which no signals are sensed; the hatched portion represents the refractory interval (RI); and the third portion represents an additional interval, the end of which time represents the end of the minimum pacing interval (MPI). An interference delay, or Noise Interval, is timed out in accordance with the linear timing portion titled "Noise", and is typically on the order of about 110 ms. However, the Noise Interval can be set at shorter or longer intervals. As seen at the start of FIG. 2C, a pace pulse is delivered, and concurrently therewith both the main escape timer and the background escape timer are reset to their full value. The two timers start to count down, illustrated as a linear downward slope toward the zero baseline. In the first cycle, the blanking period, the refractory interval and the minimum pacing interval all time out, and sometime later the main escape timer likewise times out. At this point, another pace pulse is delivered, and the same sequence is restarted. However, in this next cycle, before the main escape timer reaches zero, the sense amplifier receives a signal which is detected as a sense. The pacemaker assumes that this is a depolarization, e.g., a QRS or P wave, and resets the main escape timer. However, the background escape timer is not reset. A noise interval is initiated, and when this times out without detection of another sense, the background escape timer is reset to the same level as the main escape timer, in accordance with Rule 5. A refractory interval is timed out, corrected for the noise delay, followed by timing out of the MPI, such that the MPI is calculated to finish at the same time as though a pace pulse had been delivered at the time of the last sense. The next event that is illustrated is another sense, before the main escape timer has timed out, which resets the main escape timer and starts a new noise interval. Note that the background timer continues to count down until it reaches zero, and it stays at that level until the end of the noise interval, during which no other sense has occurred. At this time, the pacemaker logic concludes that the preceding sense was indeed a depolarization, so the background escape timer is set to the same level as then exists for the main escape timer. A new corrected RI is generated, followed by the MPI.

Referring to FIGS. 3A, B and C, which provide waveforms and a timing diagram of the same format as FIGS. 2A, B and C, there is shown the response of the pacemaker of this invention to a situation where the sense amplifer senses premature beats, or senses, each cycle. In the first cycle, a sense occurs during the refractory interval, such that there is no adjustment of either timer. The noise delay is timed out, and no other signal is sensed in the intervening time until the main escape timer counts down to zero. At this point, in accordance with Rule 9, another pace pulse is delivered, whereupon the pacemaker again schedules a blanking period, a refractory interval, and an MPI. During the second cycle, a sense occurs toward the latter part of the RI, and again a noise interval is timed out without any intervening event. The third cycle is again initiated by delivery of a pace pulse, but in this cycle the first sense occurs after the refractory interval, so that the main timer is reset (Rule 3; Rule 4). When the noise delay times out, after the end of MPI, the pacemaker logic treats the prior sense as a true depolarization, and resets the background timer to the then current value of the main timer (Rule 8). A next sense occurs during the ensuing refractory interval, and the resulting noise delay times out without any intervening event. However, the next following sense occurs after the refractory interval, but before the end of the MPI, such that the main escape timer is reset but the background escape timer is not. At the end of the following noise delay, there having been no intervening sense, the background timer is reset to the then current value of the main timer.

Referring now to FIGS. 4A, B and C, there are first shown two cycles with pulsed noise, i.e., pairs of noise signals; and then a sequence of cycles with substantially continuous noise. Referring to the first cycle, the first two signals occur during the refractory interval, the first one initiating a noise interval and the second one retriggering the noise delay without any new refractory period or additional MPI interval being set up (Rule 6). After timeout of the main timer, the same type of sense pair is detected, being different only in that the second sense occurs following the end of the refractory interval. However, since the second sense occurs before the end of MPI, no pulse can be delivered, and both timers are again reset at the timeout of the main escape interval. In the remaining cycles, eight senses are indicated, recurring following at fairly short time durations. The first sense occurs after RI, but before the end of MPI, and is initially assumed to be a depolarization. As a result, the main escape timer is reset. When the next signal occurs before the timeout of the noise delay, the pacemaker then determines that the first sense was noise. Since the second sense follows the end of MPI, a pace pulse is delivered, and both timers are reset to full value. The third sense occurs during the following refractory interval, such that the only reaction is initiation of a noise delay. The fourth sense likewise occurs during the refractory interval, and reinitiates a noise delay, as does the fifth sense. The sixth sense occurs after the end of RI, but before timeout of MPI, and since no pace pulse can be delivered, again the only reaction is resetting the noise delay. Likewise, the seventh sense occurs while the interference delay is still active, but before timeout of MPI. The eighth sense occurs while the last noise delay is still active, and since it is after the end of MPI, a pace pulse is delivered, both timers are reset, and a new blanking period RI and MPI are scheduled. Thus, the effect of continuous noise is to place the pacer in an effective inhibit mode, with pace pulses delivered subject to the exact timing of senses but at a rate not much greater than the rate corresponding to the pacemaker escape interval. The triggered rate will theoretically lay anywhere between the escape rate and the MPI rate. When there is much noise, it will approach the MPI rate.

Referring now to FIGS. 5A, B and C, the pacemaker response is shown to several different types of noise situations. The first cycle is initiated by delivery of a pace pulse, and nothing happens until a first sense after MPI. The first sense causes reset of the main timer, but not the background timer. A second sense occurs very shortly thereafter, causing the pacemaker to treat the first sense as though it were noise; a pace pulse is delivered and both timers are reset. Thereafter, there is a burst of three senses all occurring within the refractory interval, such that there is no pacemaker response. The next sense occurs before timeout of the main timer, but after MPI, such that it is treated as a depolarization (Rule 5). A noise delay is initiated, and the background timer times down to zero before the noise delay terminates. At the end of the noise delay, the background timer is set to the level of the main timer (Rule 8). Following timeout of the RI, there is a burst of five senses illustrated. The first sense is assumed to be a depolarization, and resets only the main timer, and initiates a noise delay. The second sense comes quickly, while the noise delay is active, and before the end of MPI; consequently noise is determined, so the main timer is reset to the value of the background timer (Rule 7). Each of the next three succeeding senses resets the noise delay, but no pulse is delivered since each occurs before the timeout of MPI. For each of these last three senses, there is no change in the main timer, since it is already reset to the value of the background timer. After the fifth sense, the noise interval times out without any more senses, and at the occurrence of the next sense, the main timer is reset and another noise delay is initiated. Before the noise delay times out, the background timer goes to zero. When a next sense occurs, it is outside MPI and causes a trigger pace, resetting both timers to the starting value. Note that this pace is extended a maximum of one interference delay past the end of the normal escape interval.

Figure 6A:
FIGS. 6A, B, and C are curves of the same nature as FIGS. 2A–2C for a different sequence of events, e.g., where the events constitute tachycardia.
Figure 6B:
Figure 6C:
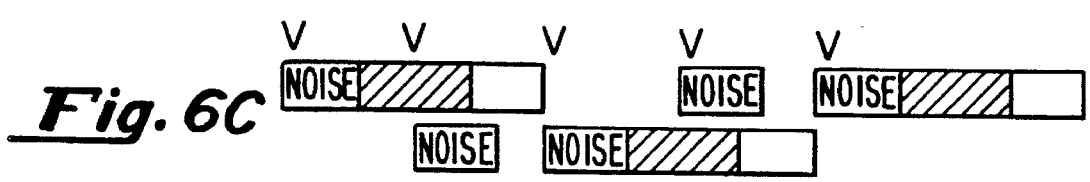

FIGS. 6A, B and C illustrate the response of the pacemaker of this invention to senses of tachycardia. In this situation, the pacemaker inhibits any pacing response by the pacemaker.

FIGS. 7A, B and C represent three cycles of a situation where there are couplets, or dual sense signals appearing very close to each other in time. In each situation, the first sense resets the main timer, and the second sense results in a pulse being delivered and each of the timers being reset.

It is to be understood that the preferred embodiments as set forth in this specification is illustrative, and that other variations are within the scope of the invention. Other criteria may be used for determining whether a sense is to be treated as a depolarization or as noise. For example, the pacemaker may also consider whether there was a sense during the refractory interval, as well as whether another sense arrives during the noise interval. For a more sophisticated pacemaker that includes rate response a physiologic historical information, e.g., phys_rate as disclosed in U.S. Pat. No. 5,247,930, certain intervals such as R.I. and MPI may be variable as a function of the sensor phys_rate.

What is claimed is:

1. A cyclically operative pacemaker system having pulse generator means for generating and delivering pace pulses to a chamber of a patient's heart, sense means for sensing signals from said heart chamber, and pulse control means operative each cycle for generating timing signals for controlling generation of pulses by said pulse generator means, said pulse control means having means for timing out a predetermined minimum time, first timer means for timing out a scheduled escape interval, second timer means for timing out said scheduled escape interval, means for resetting said first timer means to a starting value following a first sense by said sense means, noise determination means for determining whether said first sense was noise or a cardiac signal, second reset means for resetting said first timer to the value of said second timer when said first sense is determined to be noise, and safety means for controlling said pulse generator means to generate a pace pulse in response to a noise determination that occurs after time out of said minimum time.

2. The pacemaker system as described in claim 1, further comprising third reset means for resetting said second timer to the value of said first timer when said first sense is determined to be a cardiac signal.

3. The pacemaker system as described in claim 2, wherein said noise determination means comprises evaluation means for evaluating the timing of a next sense relative to said first sense.

4. The pacemaker system as described in claim 3, wherein said evaluation means comprises interval means for initiating a noise interval at the time of said first sense, and means for determining whether a said next sense occurs within said noise interval.

5. The pacemaker system as described in claim 2, further comprising fourth reset means for resetting both said first and second timer means whenever a pace pulse is delivered by said generator, and said pulse control means has first pulse means for triggering delivery of a pace pulse whenever said first timer times out said escape interval.

6. A pacemaker having pulse generator means for generating and delivering pace pulses to a chamber of a patient's heart, sense means for sensing signals from said heart chamber, and pulse control means for controlling generation of pulses by said pulse generator means, said pulse control means comprising:

escape means for timing out an escape interval;

MPI mans for timing out a minimum pacing interval (MPI);

determining means for determining whether a first sensed signal was a true cardiac signal or noise, by evaluation of any subsequent sensed signals;

trigger means for triggering said pulse generator means to generate a pace pulse when said determining means determines noise upon the occurrence of a sensed signal after time out of said MPI;

noise response means for controlling said escape means to continue to time out said escape interval when said determining means determines noise upon the occurrence of a sensed signal before time out of said MPI; and time out means for controlling said pulse generator means to generate a pace pulse upon time out of an escape interval by said escape means.

7. The pacemaker as described in claim 6, further comprising reset means to reset said escape interval to its starting value as of the occurrence of said first sensed signal when said determining means determines that said first sensed signal was a true cardiac signal.

8. The pacemaker as described in claim 7, wherein said determining means comprises noise interval means for initiating timing out of a noise interval of predetermined duration upon the sensing of said first sensed signal, and determining whether a next sensed signal occurs within said noise interval.

* * * * *